United States Patent
Eckert et al.

(10) Patent No.: US 8,706,797 B2
(45) Date of Patent: Apr. 22, 2014

(54) IMAGE PROCESSING SYSTEM FOR AN X-RAY INSTALLATION

(75) Inventors: Wieland Eckert, Fürth (DE); Rainer Krumm, Herzogenaurach (DE)

(73) Assignee: Siemens Aktiengesellschaft, Munich (DE)

( * ) Notice: Subject to any disclaimer, the term of this patent is extended or adjusted under 35 U.S.C. 154(b) by 1457 days.

(21) Appl. No.: 12/079,610

(22) Filed: Mar. 27, 2008

(65) Prior Publication Data

US 2008/0240538 A1    Oct. 2, 2008

(30) Foreign Application Priority Data

Mar. 29, 2007   (DE) .................. 10 2007 015 230

(51) Int. Cl.
*G06F 15/16*   (2006.01)
(52) U.S. Cl.
USPC ............ 709/201; 709/203; 709/248; 709/252
(58) Field of Classification Search
USPC .......................................................... 709/201
See application file for complete search history.

(56) References Cited

U.S. PATENT DOCUMENTS

| | | | | |
|---|---|---|---|---|
| 6,134,298 A * | 10/2000 | Schick et al. | ................ | 378/98.8 |
| 6,347,329 B1 * | 2/2002 | Evans | ........................... | 709/202 |
| 6,716,175 B2 * | 4/2004 | Geiser et al. | .................. | 600/450 |
| 6,859,831 B1 * | 2/2005 | Gelvin et al. | .................. | 709/224 |
| 7,047,279 B1 * | 5/2006 | Beams et al. | ................. | 709/204 |
| 7,167,762 B2 * | 1/2007 | Glanzer et al. | .................. | 700/79 |
| 7,418,470 B2 * | 8/2008 | Howard et al. | ............... | 709/201 |
| 7,552,390 B1 * | 6/2009 | Sherer | .......................... | 715/744 |
| 7,658,714 B2 * | 2/2010 | Leibig et al. | .................. | 600/443 |
| 7,672,710 B2 * | 3/2010 | Uber et al. | ..................... | 600/431 |
| 7,740,280 B1 * | 6/2010 | Moore | ............................ | 283/70 |
| 7,774,191 B2 * | 8/2010 | Berkowitz et al. | .............. | 703/23 |
| 7,894,372 B2 * | 2/2011 | Chu et al. | ....................... | 370/255 |
| 7,903,852 B2 * | 3/2011 | Springorum et al. | ......... | 382/128 |
| 7,940,699 B2 * | 5/2011 | Acharya et al. | ............... | 370/256 |
| 7,953,265 B2 * | 5/2011 | Sirohey et al. | ................ | 382/131 |
| 7,958,225 B2 * | 6/2011 | Schofield et al. | ............ | 709/224 |
| 7,983,732 B2 * | 7/2011 | Chen et al. | ..................... | 600/407 |
| 7,990,994 B1 * | 8/2011 | Yeh et al. | ....................... | 370/431 |
| 8,002,705 B1 * | 8/2011 | Napolitano et al. | .......... | 600/437 |
| 8,016,757 B2 * | 9/2011 | Kaczkowski et al. | ......... | 600/438 |
| 8,038,602 B2 * | 10/2011 | Gill et al. | ....................... | 600/121 |
| 2003/0014513 A1 * | 1/2003 | Ruths et al. | ................... | 709/223 |

(Continued)

FOREIGN PATENT DOCUMENTS

CN    1923238 A    3/2007
DE    100 04 090 C2    8/2000

OTHER PUBLICATIONS

Communication from Chinese Patent office citing reference, pp. 1-3.

*Primary Examiner* — Melvin H Pollack

(57) ABSTRACT

The invention relates to an image processing system for an x-ray installation or such like having at least one image source, a plurality of computing units for processing different algorithms, at least one non-volatile storage and a data sink, with the image source, the plurality of computing units, the non-volatile storage and the data sink each being physically connected to at least one control unit operating as a circuit module in a physical network, as a result of which a star-shaped logical topology can be configured by the control unit.

19 Claims, 2 Drawing Sheets

(56) References Cited

U.S. PATENT DOCUMENTS

| | | | |
|---|---|---|---|
| 2003/0214953 A1* | 11/2003 | El-Demerdash et al. | 370/400 |
| 2004/0078421 A1* | 4/2004 | Routt | 709/201 |
| 2005/0063575 A1 | 3/2005 | Ma et al. | |
| 2005/0080894 A1* | 4/2005 | Apostolopoulos et al. | 709/224 |
| 2006/0072800 A1* | 4/2006 | Bernard Deman et al. | 382/131 |
| 2006/0190565 A1* | 8/2006 | Ellis, III | 709/219 |
| 2007/0116037 A1* | 5/2007 | Moore | 370/462 |
| 2007/0133747 A1* | 6/2007 | Manak et al. | 378/62 |
| 2007/0167758 A1* | 7/2007 | Costello | 600/437 |
| 2007/0294333 A1* | 12/2007 | Yang et al. | 709/203 |
| 2008/0028058 A1* | 1/2008 | Shaw et al. | 709/223 |
| 2008/0030497 A1* | 2/2008 | Hu et al. | 345/419 |
| 2008/0040151 A1* | 2/2008 | Moore | 705/2 |
| 2008/0205716 A1* | 8/2008 | Von Berg et al. | 382/128 |
| 2009/0036772 A1* | 2/2009 | Lu | 600/437 |
| 2009/0083372 A1* | 3/2009 | Teppler | 709/203 |
| 2009/0175411 A1* | 7/2009 | Gudmundson et al. | 378/57 |
| 2010/0014859 A1* | 1/2010 | D'Alessandro et al. | 398/48 |
| 2010/0214313 A1* | 8/2010 | Herman et al. | 345/593 |
| 2011/0211573 A1* | 9/2011 | Perkins et al. | 370/352 |

* cited by examiner

IMAGE PROCESSING SYSTEM FOR AN X-RAY INSTALLATION

CROSS REFERENCE TO RELATED APPLICATIONS

This application claims priority of German application No. 10 2007 015 230.4 filed Mar. 29, 2007, which is incorporated by reference herein in its entirety.

FIELD OF THE INVENTION

The present invention relates to an image processing system for an x-ray installation or suchlike.

BACKGROUND OF THE INVENTION

In an x-ray system for angioplasty (angiography), a sequence of x-ray pulses is generated, with which the human body is radiated. In an image recording system (image amplifier, flat screen detector or suchlike) an 'image' is generated for each of these x-ray pulses using technical means, said image corresponding to the degree of x-ray absorption. Further sources for such image sequences can also originate from memory units or external signal sources (also other modalities such as MR, CT, ultrasound . . . ). In the further sequence, these digital x-ray images are processed in an image processing system (IPS), with different algorithms being used for image enhancement purposes. The images thus processed are in turn output in a temporal sequence on a monitor for diagnosis purposes.

It is characteristic of an IPS that the frequency of the x-ray pulses is fixed or variable and typically moves in a range of between 1 to 60 images per second. A prerequisite for an IPS is that only a specific predetermined time span may elapse, the so-called latency of the IPS, from the image information arriving from the image recording system until this image is displayed on the monitor.

An IPS further requires image data of the current examination to also be able to be simultaneously stored on a non-volatile storage (e.g. hard disk). At a later point in time, this image data can then be reprocessed by different algorithms of the IPS, if necessary also by algorithms other than those during the original recording, or in a different parameterization of the algorithms, with the original image repetition rates having in turn to be maintained. A further application also considers the reproduction at a higher or lower speed.

A typical application is shown in FIG. 1, which illustrates an IPS as claimed in the prior art. An image source BQ allocates different algorithms to different computing units PE1, PE2.1, PE2.2, PE3.1, PE3.2, PE4 as well as to a memory and finally to a data sink DS.

The following difficulties arise with such an implementation of such an IPS shown in FIG. 1.

The duration for the calculation of the individual algorithms may be very different. Differences of one or more decimal powers can easily exist in the required computing time between the individual algorithms.

The overall computing power required to execute the algorithms is very high. This can generally no longer be achieved by one single processor.

The division on a multiprocessor system is not a trivial matter. Due to the strict timing of the input image data, a rigidly clocked system is generally used, with the timing corresponding to the image sequence frequency and/or a multiple or fraction thereof.

In different applications, the configuration of the processing chain can indicate clear differences, for instance when the data does not come from the image recording system (live) but instead from the non-volatile storage (replay).

As a result of the high level of computing power required, a so-called "customer-specific circuit" (ASIC) is particularly suited to implementing the algorithm. The effort involved in designing such a circuit is enormously high and the production costs only depreciate with very high quantities. Such a circuit cannot be changed afterwards, for instance when an improved algorithm has been found.

With the realization in a programmable logic module (FPGA), the depreciation of the costs is already achieved with a significantly lower quantity. The development costs are also considerably lower than with an ASIC. However, the expandability of the algorithms is significantly restricted by the predetermined number of available logic elements in an FPGA. The design of the logic is not very simple and is only controlled by specialists.

The use of programmable processors (universal processor CPU or signal processor DSP) achieves a significant simplification. A number of processors, which process the image data, is typically used with an IPS. The necessary computing power is herewith achieved in that the overall task is distributed across several processors. A pipeline of processes is frequently established here, as is shown in FIG. 1. The known techniques for using several processors are the sequencing of processing steps and the division of data into several similarly-operating processing stages (striping), with the individual partial results being combined again by means of interleaving.

The computing units PE1, PE2.1, . . . (Processing Elements) shown in FIG. 1 can be different computing units, such as for instance ASIC, FPGA, DSPs, universal processors, microcontrollers, routers, periphery controllers and suchlike. In the previous methods of resolution, of which the arrangement shown in FIG. 1 is an example, a specific topology of the data flow is established by physically connecting the individual PEs. The allocation of the algorithms to the computing units is carried out in a design phase, in which the topology, the computing power, the data transfer and the demand for latency of the individual stages as well as the overall processing have to be taken into account. The previous approaches have generally resulted in a direct mapping of the algorithms on assigned PEs, as is the case in the design shown in FIG. 1. This direct allocation is normally regarded as a 'natural' realization of the sequence of algorithms. Accordingly, the data paths are established and direct connections between the PEs are established.

SUMMARY OF THE INVENTION

The object underlying the present invention is to improve an image processing system such that it can adjust significantly more flexibly to new algorithms, does not have higher latency and can be manufactured in a simpler fashion, thus rendering it more cost-effective.

This object is achieved by the features of the independent claim.

Features of preferred embodiments of the present invention are characterized in the dependent claims.

The new approach of the present invention relates to an architecture of a "packet switched network". The central element of this architecture is a module ("switch" module), which can route data streams from and to the connected users, with these data streams not inhibiting one another. The data streams are regarded as a temporal sequence of elementary units, the so-called data packets. Packet-switching "switches" can be established using different methods and protocols. Ethernet, InfiniBand or RapidIO are widespread for instance. It is essential here that a physical line is not connected between the users, with only the payload data being transmitted, but that the sender and receiver information and further management information is also added to each data packet, said information being necessary and/or useful in order to forward the packets from the sender to the receiver. This produces the physical topology of a star.

By interconnecting several "switches", a hierarchical star can also be established, with this being regarded as a simple star by the communication of the "switches" with one another. In this way, the same mechanism for data transfer is maintained by all the users involved.

BRIEF DESCRIPTION OF THE DRAWINGS

The invention is described in more detail on the basis of the description of exemplary embodiments with reference to the drawings, in which.

DETAILED DESCRIPTION OF THE INVENTION

Figure 1:
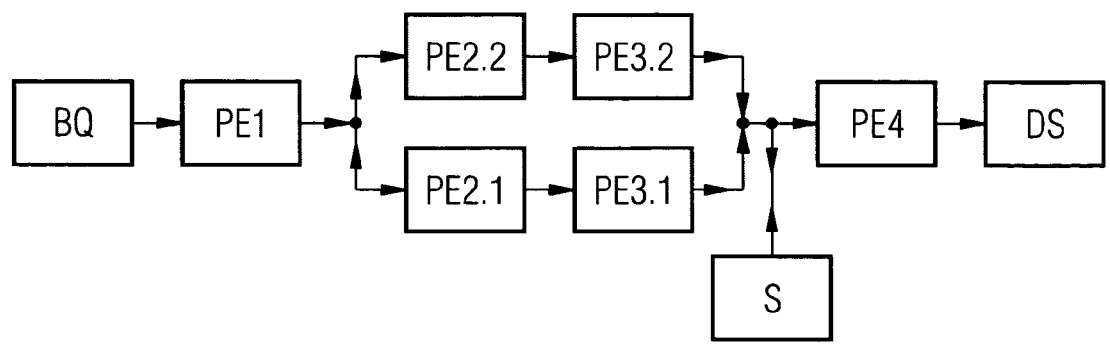
FIG. 1 shows the design of a conventional image processing system.
Figure 2:
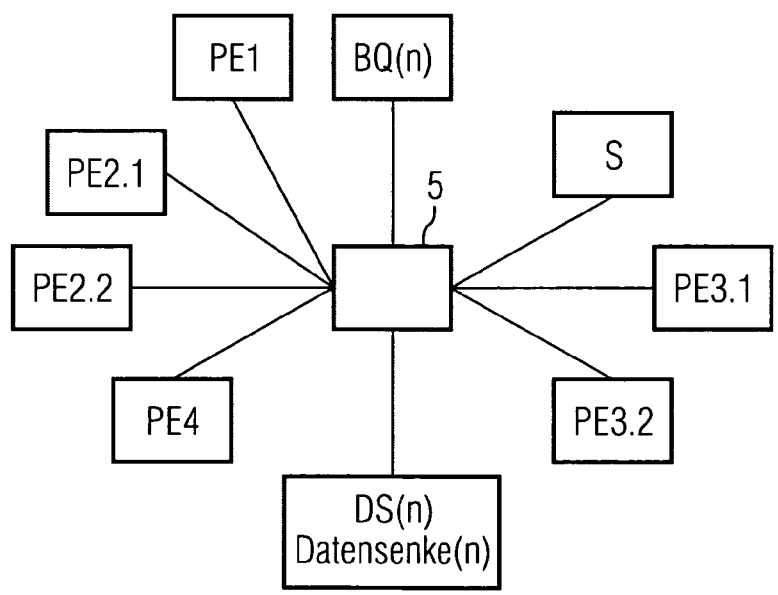
FIG. 2 shows the star topology of a first exemplary embodiment of an image processing system according to the invention.

As FIG. 2 shows, the individual components of the image processing system, i.e. the image source and/or image sources BQ(n), the computing units PE1, PE2.1, . . . , a memory S and a data sink and/or data sinks DS(n) are arranged around a control unit 5 in the manner of a star. In an initial configuration step, the desired logical topology is applied to the image sources, computing units, memories, and data sinks, i.e. the incoming and outgoing data streams of the user as well as the complexity of these streams are defined in the "switched network". All data transfers ideally take place over this "switched network", which typically has a very high switching capacity as a result of the simple task.

The individual arithmetic units can also be seen as a "pool", from which, depending on the application, the necessary units can be interconnected to one another by means of corresponding data streams. In this way, the arithmetic units are also adjusted to their respective tasks (algorithms) by the control unit. The "logical topology" of the processing stages is determined by this configuration process. With the solution according to the invention, the additional possibility is however created in that the allocation of the algorithms to the arithmetic units and the allocation of the data streams from application to application can be different. The image processing system according to the invention is a rigid structure, in which at the time of design, it has to be precisely determined which algorithms are to be used, which type and realization of the PEs is to be used (type, characteristics) and which interconnection of the PEs with one another is to be carried out.

In accordance with the invention, the data streams are regarded as temporally changeable structures, which also require a temporally changeable interconnection of the PEs. The most important discriminator is the dynamic reconfiguration of the architecture of the image processing system according to the invention, with the aspects of the subsequent modular expandability and the evolution with the advancing development of the processing algorithms being a priority.

The most important characteristic of the image processing system according to the invention is its configurability. Whereas with the previously proposed solutions, the physical topology and logical topology were identical, with the image processing system according to the invention, these can be different. The separation of the logical and physical configuration was hitherto not possible.

It is also possible to design the logical topology differently as a function of the application, i.e. the architecture can be reconfigured dynamically. Whereas with the previous solutions, these different applications had to be known and taken into consideration during the design of the physical topology, another logical linking can now also be carried out at a later point in time. This can be necessary for instance if an algorithm is improved and now has to be distributed between more computing units as a result of the increasing demand for computing power. The "field upgrade" of the algorithms is herewith designed to be considerably more flexible. In particular, there is also the possibility with this architecture to add an additional algorithm to an existing chain of processing steps, said algorithm not having been provided within the original design. This is not possible with a rigid physical interconnection. In the image processing system according to the invention, this is enabled by a changed interconnection (routing) of the data streams in the switched network, i.e. in the control unit 5. The image processing system according to the invention can be expanded in a modular fashion, also beyond the original intended use of the image processing system. If new or changed algorithms require an extensive redesign of the computing power, this can be carried out in a simple and modular fashion. If necessary, even the "hot-plug" is possible as a function of the selected switching technology, such as is known and common practice for instance with Ethernet-based networks. After the control unit has recognized these additional computing units, they are used if necessary.

Figure 3:
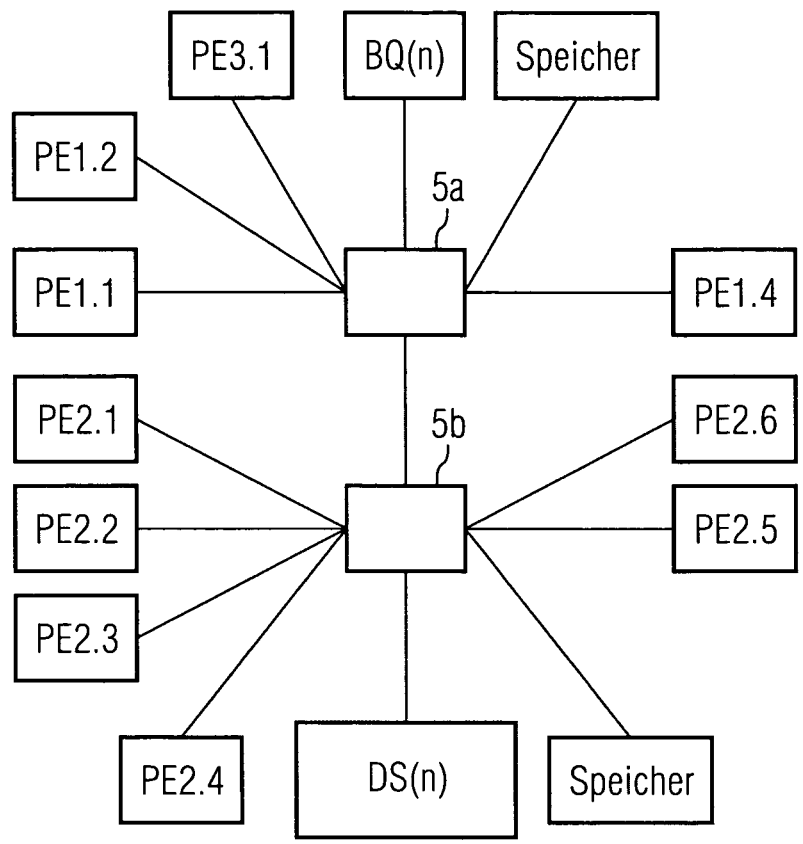
FIG. 3 shows the topology of a second exemplary embodiment of the present invention.

FIG. 3 shows a cascading of control units 5a, 5b and the modular design of a network as a second exemplary embodiment of the present invention. A control unit has a certain capacity, both in respect of the number of connectable users (number of ports), as well as in respect of the switching capacity ("packets per second" or "bits per second"). The realization of an image processing system based on this architecture need not be attuned to the possible maximum design, i.e. the number of ports, from the outset, but can however be extended under certain circumstances at a later point in time to include further control units. In this way, the switching capacity of the switches, i.e. of the control units, is to be noted and accounted for in the logical topology. As FIG. 3 shows, a second control unit 5b is arranged downstream of the control unit 5a, from which connections go to the individual computing units PE2.1, PE2.2 . . . , to a further memory and to the data sink DS in a star-shaped fashion.

In addition to the possibility of a direct connection ("point-to-point"), the control unit can also implement a duplication ("point-to-multipoint", "multicast", "broadcast") of the data packets, with different receivers obtaining this duplicated data. The extraction of data streams from the internal connection can be used for different purposes, for instance for fault finding in the laboratory, for the purpose of monitoring in the field, or quite simply for differently further processing the same original data. The latter case may apply if a data stream for representation by means of video signals (BAS inter alia) or a recording on the VCR/DVD is to be calculated from the running image sequence, which is present in the higher local resolution, said data stream being required in another (lower) local resolution. The realization of this "T-piece" for extracting the data stream can be implemented in a simple fashion within the control unit, without affecting the primary transmitter or receiver of the data stream. No changes are then necessary for these components, since the overall interconnection and duplication of data is carried out in the control unit.

In the case of a defective computing unit, a replacement unit which is potentially available can only be used in a simple fashion by changing the logical connections. Although in the case of a sudden failure of a unit, the current processing can probably not be continued without any interferences, the possibility still exists of reestablishing the entire processing topology by means of a standby module. The service time is herewith reduced and the availability of the installation is improved. Similar methods are known from RAID hard disk systems. The defective unit can be exchanged at a later point in time.

Figure 4:
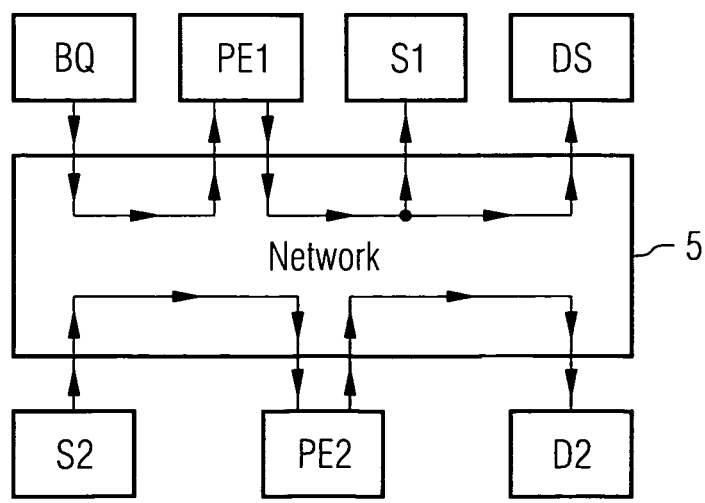
FIG. 4 shows the topology of a third exemplary embodiment of the present invention.

The known realizations of "switched networks" even allow different logical networks to be realized on a physical network ("virtual private network", VPN). In this way, the underlying control units already ensure that the VPNs are not able to inhibit one another. The defensive security is reliably provided in advance. Bandwidths can also be distributed to these VPNs. The functionality and safety is ensured by means of the configuration of the network, even if certain users do not adhere to specifications due to a malfunction for instance. FIG. 4 shows an example of two logical networks in a physical network. The separation of the logical network is only to be established during the initial configuration and is then not to be taken further into consideration for the network user.

Furthermore, with a "packet switched network" architecture, the logical interconnection of the data streams are adjusted to this, so that otherwise idle computing units can be used for other purposes.

With a simple realization, a computing unit can also take over the function of a control unit module. In this case, the switching-functionality is thus not taken over by a dedicated module, but is instead implemented by the computing unit itself. It is characteristic of such an arrangement for the computing unit itself to then be equipped with several ports and for the switch functions to herewith be able to be realized. A separation of the switching and computing tasks is not imperative. Generalization of this concept also allows the direct connection of two computing units to be considered as such a network, provided the transmission is carried out in the form of switching-capable data packets. A large network is not necessarily needed to fulfill the definition of the present invention here. One example of such a degenerated network are the realizations of "PCI-Express"-based architectures (PCIe), with switching components present in the star point frequently being coupled very closely to one of the computing nodes (co-location) and thus taking over control functions. These realizations thus typically also show a relatively small growth with few network nodes. An expansion to larger network topologies then provides for the technology "PCIe advanced switching", which compensates for the restriction to singular star topology and thereby enables larger networks.

Finally, the 'switched network' architecture results in the new possibility that a computing unit which is not fully loaded takes over additional calculations, which do not accumulate in direct proximity. This is enabled by a further data stream being conveyed to the computing unit and the results being routed further via the control unit. The allocation of the algorithms is no longer related to the physical topology of the image processing system, as with the pipeline architecture as claimed in the prior art.

The possibility of routing the data streams to the computing units allows new prospects with the expansion of the processing chain in the image processing system according to the invention to result. The possibility is herewith created of attaching parallel streams, which were not present in the original design of the image chain. The "switched network" architecture allows this in a simple fashion by means of configuration of the network and computing units. In particular, the injection (and if necessary the subsequent extraction) of data streams of a different origin is herewith also possible. Thus the fusion of data material from other modalities (e.g. magnetic resonance, computer tomography) can then be considered at a later point in time and does not have to be completely defined and released with the first design of the processing chain. These external data streams can pass through a completely different processing in order then to finally be related to the image data. These references can be produced by different indicators (e.g. time information, time stamps, local information, other features) and do not necessarily have to be carried out by the timing inherent in the image chain. In a rigid image pipeline system as claimed in the prior art, such a coupling is not possible.

The afore-described preferred embodiments of the present invention can be combined with one another in any fashion. For instance, a computing unit in two VPNs of non-interrelated stages of the processing etc. can take over. The developer of an image processing system according to the invention can use all these possibilities taking into consideration the demands for fail-safety and throughput.

The invention claimed is:

1. A non-transitory image processing system for an x-ray installation, comprising:
    an image source comprising image sequences from a sequence of x-ray pulses to be enhanced according to an image processing application;
    a plurality of computing units for processing images in accordance with different imaging processing algorithms allocated to respective computing units;
    a memory;
    a data sink; and
    a control unit physically connected to elements comprising the image source, the plurality of computing units, the memory, and the data sink in a physical network having a star-shaped topology, with the control unit located centrally in the star-shaped topology and the elements branching therefrom, forming a switched network;
    wherein the control unit operates as a circuit module in the switched network and is adapted to realize different logical topologies for the elements by allocating different imaging processing algorithms to respective computing units according to the image processing application for image enhancement purposes and routing data streams between computing units in a desired processing sequence for imaging processing as a chain of processing steps irrespective of the topology of the physical network, so that a desired logical topology interconnecting the computing units is dynamically configured by the control unit as a function of the image processing application.

2. The image processing system as claimed in claim 1, wherein the circuit module is adapted to convey data streams as a temporal sequence of data packets, the data packets having emitter and receiver information added with a protocol.

3. The image processing system as claimed in claim 2, wherein the protocol is selected from the group consisting of: Ethernet, InfiniBand, and RapidIO.

4. The image processing system as claimed in claim 2, wherein the circuit module is adapted to add further management information to the data packets.

5. The image processing system as claimed in claim 2, wherein the data streams and a physical and logical interconnection of the image source and the computing unit illustrate temporally changeable variables.

6. The image processing system as claimed in claim 1, further comprising one or more further control units operating as circuit modules to which the image source, the plurality of computing units, the memory, and the data sink are interconnected as a hierarchical physical star topology.

7. The image processing system as claimed in claim 6, wherein the circuit modules are configured one behind the other in a cascade connection.

8. The image processing system as claimed in claim 1, wherein the circuit module is adapted to broadcast duplicate data packets directly to different receiving computing units.

9. The image processing system as claimed in claim 1, wherein the control unit is adapted to activate a replacement computing unit by changing a logical connection in the logical topology.

10. The image processing system as claimed in claim 1, wherein the control unit is adapted to configure a plurality of different logical topologies at a same time in the physical network.

11. The image processing system as claimed in claim 1, wherein one of the plurality of computing units comprises a plurality of several ports and functions as the control unit operating as the circuit module.

12. The image processing system as claimed in claim 1, further comprising a plurality of computing units directly connected to one another.

13. The image processing system as claimed in claim 12, wherein two or more of the computing units are directly connected to one another.

14. The image processing system as claimed in claim 1, wherein the image source inputs or outputs data from an image modality.

15. The image processing system as claimed in claim 1, wherein the star shaped physical topology is different from the logical topology.

16. The image processing system as claimed in claim 15, wherein the physical topology is modularly expanded.

17. The image processing system as claimed in claim 16, wherein a "hot-plug" technology is used for the expansion.

18. The image processing system as claimed in claim 16, wherein an allocation of an algorithm that is processed by the computing unit is not related to the physical topology.

19. A method for installing an x-ray imaging processing system, comprising:
   providing an image source comprising image sequences from a sequence of x-ray pulses to be enhanced according to an image processing application;
   connecting a control unit with elements comprising the image source, a plurality of computing units for processing images in accordance with different imaging processing algorithms allocated to respective computing units, a memory, and a data sink in a physical network having a star-shaped topology, with the control unit located centrally in the star-shaped topology and the elements branching therefrom, forming a switched network;
   operating the control unit as a circuit module in the switched network adapted to realize different logical topologies for the elements, the control unit for dynamically configuring a desired logical topology according to the image processing application;
   allocating different imaging processing algorithms to respective computing units by the control unit according to the image processing application for image enhancement purposes; and
   routing data streams between computing units in a desired processing sequence for imaging processing as a chain of processing steps irrespective of the topology of the physical network by the control unit, so that the desired logical topology interconnecting the computing units is dynamically configured by the control unit as a function of the image processing application.

* * * * *